(12) United States Patent
Sharkey et al.

(10) Patent No.: US 6,436,129 B1
(45) Date of Patent: Aug. 20, 2002

(54) METHOD AND APPARATUS FOR STIMULATING NERVE REGENERATION

(75) Inventors: Hugh Sharkey, Woodside; Bruno Strul, Portola Valley, both of CA (US)

(73) Assignee: Oratec Interventions, Inc., Menlo Park, CA (US)

( * ) Notice: Subject to any disclaimer, the term of this patent is extended or adjusted under 35 U.S.C. 154(b) by 0 days.

(21) Appl. No.: 09/488,161

(22) Filed: Jan. 20, 2000

Related U.S. Application Data
(60) Provisional application No. 60/116,724, filed on Jan. 20, 1999.

(51) Int. Cl.$^7$ .................................................. A61F 7/00
(52) U.S. Cl. .............................. 607/96; 607/2; 607/50; 607/88; 607/100; 607/101
(58) Field of Search ............................ 607/96, 50, 118, 607/89–91, 88; 606/2–3, 10, 11

(56) References Cited

U.S. PATENT DOCUMENTS

| | | | |
|---|---|---|---|
| 5,190,539 A | | 3/1993 | Fletcher et al. ............ 606/25 |
| 5,445,146 A | * | 8/1995 | Bellinger ................ 607/89 |
| 5,464,436 A | * | 11/1995 | Smith ..................... 607/89 |
| 5,584,885 A | * | 12/1996 | Seckel ................... 623/11 |
| 5,601,618 A | * | 2/1997 | James .................... 607/71 |
| 5,638,830 A | | 6/1997 | Valade ................. 128/897 |
| 5,656,605 A | * | 8/1997 | Hansson et al. ........... 514/21 |
| 5,755,752 A | * | 5/1998 | Segal .................... 607/89 |
| 5,827,271 A | | 10/1998 | Buysse et al. ............. 606/40 |
| 5,951,596 A | * | 9/1999 | Bellinger ................ 607/89 |
| 6,033,431 A | * | 3/2000 | Segal .................... 607/89 |
| 6,095,148 A | * | 8/2000 | Shastri et al. ............ 128/898 |
| 6,273,905 B1 | * | 8/2001 | Streeter ................. 607/89 |

FOREIGN PATENT DOCUMENTS

| | | | |
|---|---|---|---|
| WO | WO 97/36548 | 10/1997 | .......... A61B/17/39 |
| WO | WO-97494-53 | * 12/1997 | |
| WO | WO-97/49453 | * 12/1997 | |

OTHER PUBLICATIONS

M. Weiss et al., "Effect of Thermal Stimuli on Post Traumatic Growth of Peripheral Nerves" Balneoligia Polska, vol. 16, Mar. 2, 1971, pp. 151–153.

* cited by examiner

Primary Examiner—Michael Peffley
Assistant Examiner—Pete J Vrettakos
(74) Attorney, Agent, or Firm—Fish & Richardson P.C.

(57) ABSTRACT

A method is provided for stimulating nerve growth, especially for nerve regeneration after damage to the nerve. The method comprises: applying thermal energy to one or more nerve segments adjacent a damaged region of the nerve, such that nerve fibers from the treated adjacent segment are stimulated to grow and extend toward the damaged region. The method may be used to enhance mechanical stimulative effect at a terminus of a severed nerve or a region of nerve injured by crush or other physical forces. The method may also be used to treat nerve segments retrograde up the nerve fiber and to increase the response of the injured nerve to regrowth and extension rapidly. An apparatus for delivery of thermal energy to the distal terminus of the severed nerve or region is disclosed. Thermal conductive or electromagnetic energy is delivered through a probe having a handle and a shaft. An energy delivery portion of the probe is configured to apply thermal energy to the distal segments of the severed nerve to promote rapid and more extensive growth of the nerve cells.

20 Claims, 4 Drawing Sheets

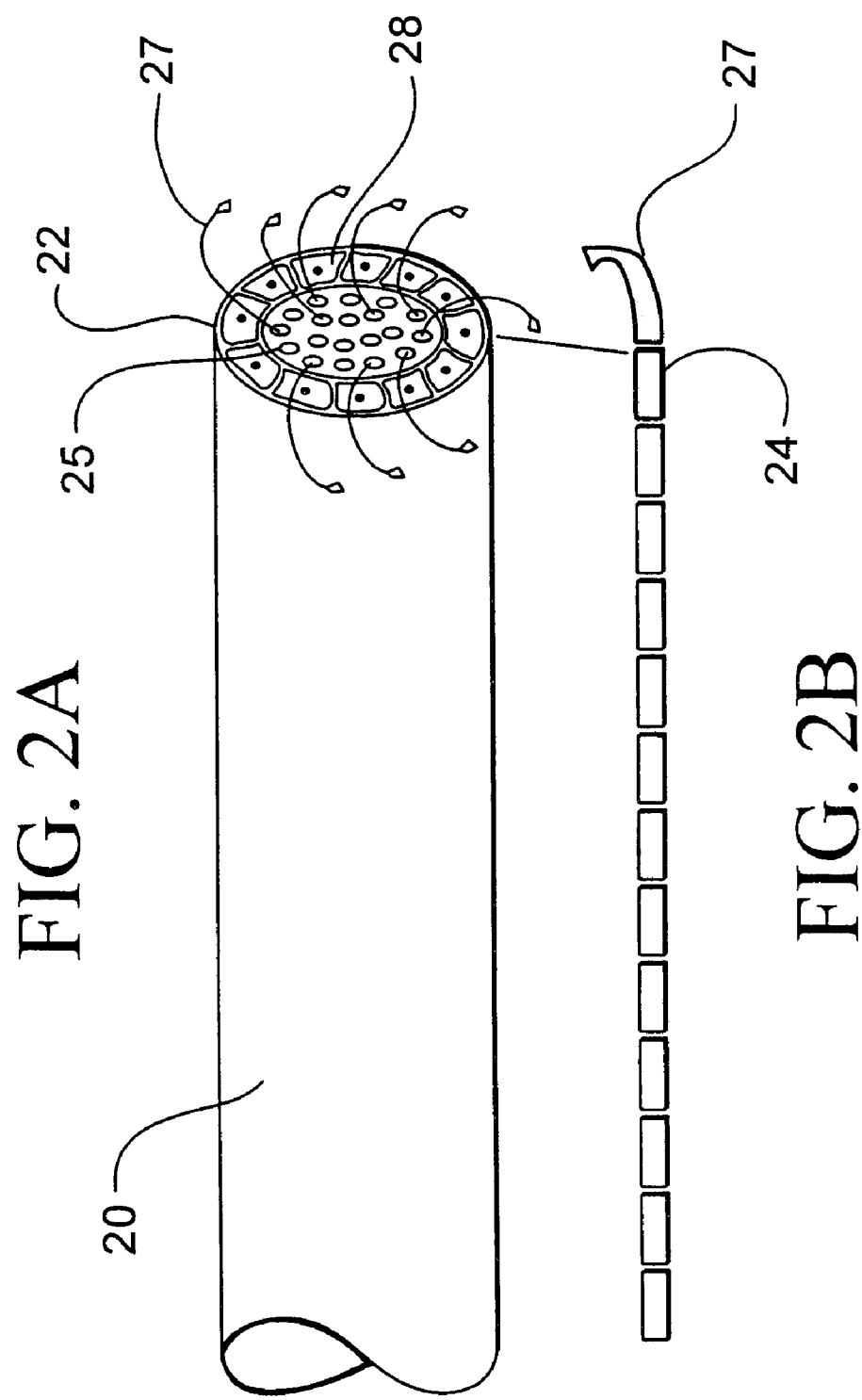

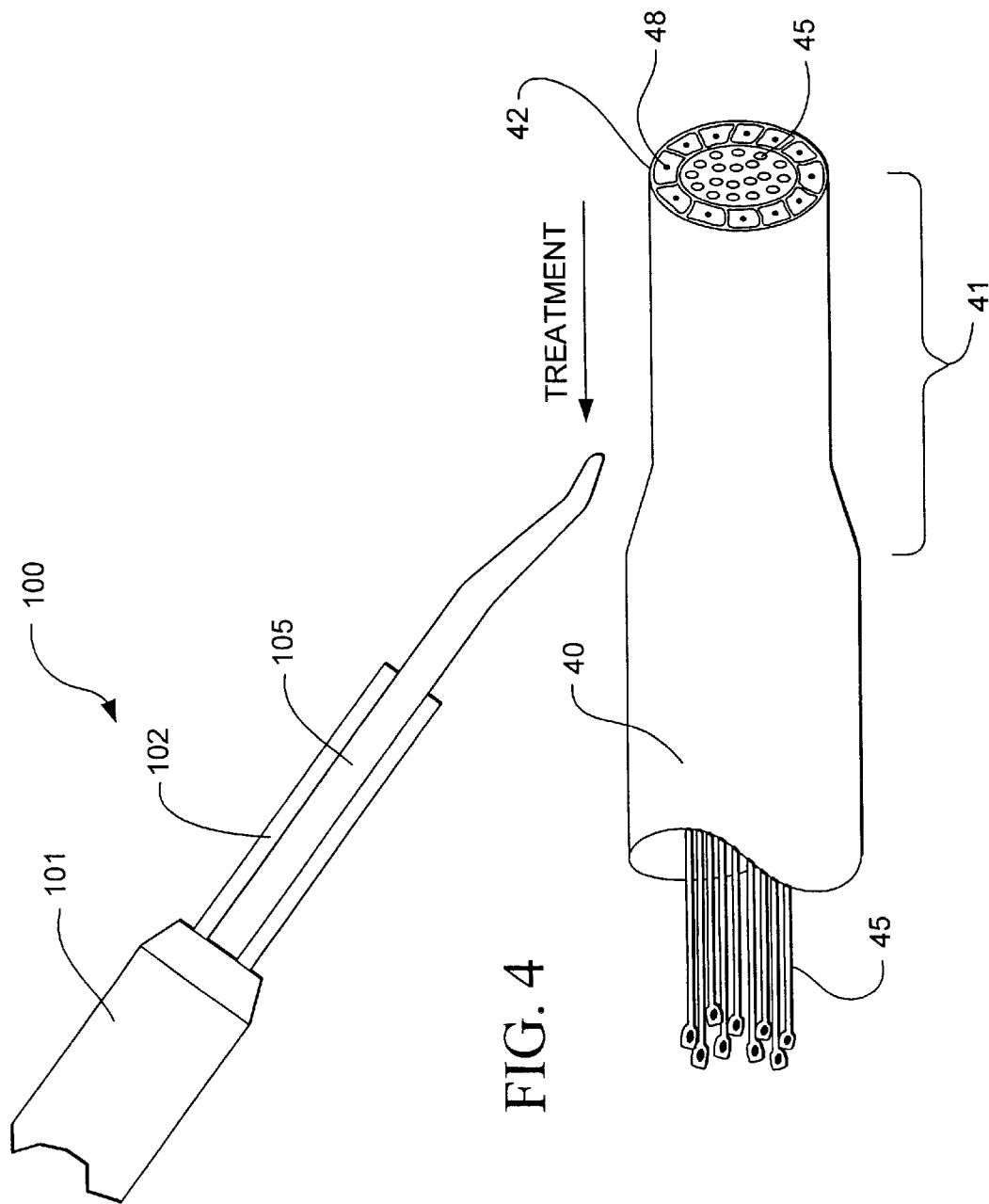

METHOD AND APPARATUS FOR STIMULATING NERVE REGENERATION

RELATIONSHIP TO COPENDING APPLICATIONS

This application is a continuation-in-part of "METHOD AND APPARATUS TO STIMULATE NERVE REGROWTH," Provisional Application Serial No.: 60/116,724; Filed: Jan. 20, 1999 which is incorporated herein by reference.

BACKGROUND OF THE INVENTION

1. Field of the Invention

The present invention relates to methods and apparatus for enhancing nerve regeneration and growth, and more particularly relates to a method and apparatus for stimulating axon and dendrite extension across a severed nerve section.

2. Description of Related Art

The peripheral and autonomic nervous system are formed by nerve cell bodies and processes, i.e., axons and dendrites forming bundles, innervating the skin, skeletal muscles, glands and related structures. The nerve cell bodies are situated in the brain, spinal cord or in ganglia. Each myelinated nerve fiber is enveloped by Schwann cells. In the case of unmyelinated fibers, several axons are enclosed in each Schwann cell. The Schwann cells are enveloped by a basement membrane, an extracellular matrix and an endoneurial mesenchymal sheath. Many such units form a nerve, which is limited by a perineurium of collagen, fibroblasts and related cells. An epineurium encloses the entire nerve, mostly comprising several nerve fascicles. A blood-nerve barrier prevents plasma proteins and many other substances from unrestricted penetration among the nerve fascicles. Motor and sensory nerves have the same structure but differ with regard to the axon and myelin dimensions. This means that in a mixed peripheral nerve it is not possible by the morphological characteristics to state whether a single axon is afferent or efferent. Autonomic nerve fibers, sympathetic and parasympathetic, are accompanying the sensory and motor nerve fibers as well as blood vessels.

Nerve cells and their supporting neurological cells are derived from the neuroectoderm. Although originally having a common embryonic origin, the nerve cells at an early state differentiate and obtain their structural characteristics. About four decades ago Hamburger and Levi-Montalcini demonstrated that the development of neurons are dependent on their target structures in order not to degenerate after differentiation. They provided direct evidence that neurons may die during normal development if not gaining synaptic contacts. This is true both for the central, peripheral and autonomic nervous systems.

The nerve cells in the central and peripheral nervous system reach their final number at about birth in mammals. The regenerative capacity present for peripheral and autonomic nerves during childhood is reduced with increasing age. This means that no new nerve cells are formed after birth, although axons and dendrites may regenerate to a limited extent. The autonomic system has a much higher regenerative capacity than the peripheral nervous system.

Injury to peripheral and autonomic nerves results in degeneration of the distal parts of the axons and dendrites. After dissection, Wallerian degeneration results in hypertrophy and hyperplasia of the Schwann cells lining the distal nerve. The proximal end of the injured axons retract to a variable extent, and, after a short lag period, the repair processes of the nerves begin.

Sprouts with finger-like extensions form a leading part of the outgrowing cell processes, the path of which is guided by the reactive Schwann cells. In most systems the rate of regeneration is in the range of 1–2 mm/day. Higher values have been documented for the autonomic nervous system. However, after about a month, depending on the test system examined, the rate of regeneration begins slowing down and eventually ceases. Little is known about the mechanisms which regulate the rate of regeneration. Detailed mechanisms of the regenerative process remain unknown.

Nerve crush is an injury of moderate severity, mostly resulting in complete recovery of the structure and function of injured axons and dendrites. It has been established that continuity of the basement membrane as well as early reestablishment of the microcirculation in peripheral nerves after crush injury is a prerequisite for complete recovery. Discontinuities in the basement membrane or even limited persistent blood vessel damage delay or impair the recovery.

Sectioning of a nerve results in discontinuity of the epi-, peri- and endoneuriums, as well as of the basement membrane enveloping the supporting Schwann cells with the enclosed axons and dendrites. Extensive vascular damage occurs as well. In the latter cases nerve regeneration starts after a delay of a few days in most clinical and experimental systems using peripheral nerves. Even meticulous microsurgery, almost reestablishing continuity of each nerve fascicle to each corresponding nerve fascicle by approximation, is not sufficient to gain any major improvement of the regeneration. Removal of the peri- and/or epineurium neither improves the extent of nerve regeneration, structurally or functionally. Most techniques used result in limited improvement as compared to if the nerve ends remained opposed. For example, further complications which occur in cases of sectioned peripheral nerves are the formation of neuroma and fibrous scar tissue starting after about a week. This eventually results in formation of neuroma and a permanent deficient function of the nerves. In the case of physical separation of peripheral nerves, the severed distal segment begins the process of Wallerian Degeneration soon after severing if microcirculation and reapproximation of the severed segment does not occur.

Adequate function of the target innervated by peripheral and autonomic nerves seems to be a prerequisite for maintenance of the function of the peripheral and autonomic neurons. Hamburger, et al. established that neurons depend on their targets for their survival. This means that damage to skeletal muscle cells, integumentum or glands result in disconnection of synapses from the target organ and more or less extensive degeneration of at least the distal parts of axons and dendrites. The degeneration may be of such extent that even neurons are lost. Recovery of the target organ may result in recovery of function after appropriate regeneration. Even in such cases, continuity of the fascicles, at least to the close vicinity of the target organs, and adequate microcirculation seems to be a prerequisite for successful regeneration.

As described in detail above, nerves are vital to the basic operation and function of the human body. Injury to a nerve can result in a partial or total loss of the sensation, control, or use of a member or portion of the body. Although methods currently exist for surgically repairing nerve tissue, such methods are not always possible and are commonly not completely successful in achieving a restoration of sensation, control, and use of the affected portion of the body.

One method for repairing served nerve involves the use of very fine sutures (multiple microsutures) to sew the severed nerve ends together. Such microsurgical procedures are typically conducted with the use of a microscope, which is tedious and time-consuming. Further, such microsurgical procedures are often not very successful, particularly in view of the large amount of time which typically transpires before surgery can be completed, as well as in view of the amount of manipulation which is required while the ends of the injured nerve are being meticulously sewn together using these microsurgical techniques. In addition, the improvement may be limited in spite of careful microsurgical reestablishment of connections between the nerve ends, presumably because reestablishment of close contact of severed nerve ends is not enough for successful nerve regeneration.

Where substantial nerve injury has occurred, it is often physically impossible to suture the severed nerve ends together. Thus, for more extreme nerve injuries, nerve grafts are often used as a nerve replacement. However, suture techniques and/or grafting have not always been sufficient for repair of a severe defect. Furthermore, suture under tension, gap reduction by stretching, mobilization, flexion of a joint, or rerouting may compromise sensitive intraneuronal vascularity, and autografts induce a second surgical site with requisite risks and complications. Moreover, in many instances, there was either no nerve growth or only growth of connective tissue. Thus, the functional results of surgical repair of peripheral nerve injuries have been disappointing in spite of improved surgical techniques.

Several techniques have been established since the pioneering work almost a century ago by J. Forssman, who demonstrated improved regeneration of peripheral nerves by using a reed as a guide. After that, several similar devices have been assigned, aimed to improve the nerve regeneration. Lundberg and Hansson (Brain Res 178, 573-576, 1979) developed a technique using a pseudomesothelial-lined chamber which obviously improved to some extent the nerve regeneration.

Conduits of various types have been investigated which consist of tubes of various composition (e.g. collagen, fascia, etc.) that are employed to act as a guide for nerve growth down a defined track in an attempt to promote anatomic reanastomosis by normal physiological procedures. Silicon tubes and tubes of biodegradable material have also been developed and extensively used.

These techniques seem to improve the initial outcome of the nerve regeneration, mostly due to a reduction in the extent of neuroma formation. In several reports significant although minor improvements could be demonstrated with regard to the number of nerve fibers reestablishing contact as well as increase in myelination and diameter of the axons. Unfortunately, a considerable proportion of the nerve fibers fail or cease to regenerate, and do not establish synaptic contacts. There is little to no difference between motor nerve fibers and sensory ones. This means that although structural contacts may be reestablished, deficiency in function persists. Furthermore, the greater length of time taken for the nerve regeneration results in atrophy and even extensive degeneration of target tissues such as skeletal muscles and skin structures, including glands and receptors. Thus, the longer the distance and the more extensive the damage, the benefits obtained using these technique for improving nerve regeneration have been minor.

Schwann cells in reactive nerves, injured by sectioning or by crush, exert positive influence in improved regeneration of peripheral nerve fibers. Crush of a nerve 2 weeks prior to a second injury results in improved regeneration as compared to non-primed nerves. Similarly, the use of a distal sciatic nerve as a target in conduit methods improves the regeneration of the sciatic nerve in rats. Predegeneration of the target nerve by injury one or 2 weeks prior to reestablishment of contact thus induces formation of factors seemingly improving long-term degeneration. Several different experimental systems have been established by various groups during the last decades (Sjoberg, J. and Kanje, M. (1990) Brain Res. 530:167–169). However, no specific factors have yet been identified or demonstrated to be responsible for the improved nerve regeneration.

SUMMARY OF THE INVENTION

The present invention provides a method and apparatus to stimulate regrowth of damaged nerves, in particular and to cause nerve fibers to extend and bridge a severed nerve section. The method for promoting regeneration of a damaged nerve comprises applying thermal energy to one or more nerve segments adjacent a damaged region of the nerve, such that nerve fibers from the treated segments are stimulated to grow and extend toward the damaged region. The damaged region of the nerve can be a terminus of a severed nerve or a region of a crushed nerve.

Various energy sources may be used to provide the thermal-mechanical stimulation of the nerve segment adjacent the damaged region, preferably thermal energy from thermal conductive or electromagnetic sources at low energy levels. Examples of thermal conductive energy sources include but not limited to resistive heating. Alternatively, the thermal energy may be generated by ultrasound. Examples of electromagnetic energy sources include but are not limited to radio frequency (RF) energy, coherent light, incoherent light, microwave and shortwave.

For example, thermal energy generated from a resistive heating source may be applied directly to opened segments of the damaged nerve. Alternatively, thermal energy may be applied superficially to treat the segments adjacent the damaged region of the nerve.

The one or more treated segments may be a nerve segment adjacent to the damaged region, preferably 1–18 mm, more preferably 2–15 mm, and most preferably 2–10 mm from the damaged region. Alternatively, the one or more treated segments may be a plurality of nerve segments located in region adjacent the damaged region, preferably in a region 5 mm to 20 mm distal to the damaged region.

The thermal energy applied to the segments of nerve adjacent the damaged region may be of a sufficient amount for heating the segments to a temperature in a range about 41–58° C., preferably about 44–55° C.

A guide template may be placed over the damaged region to direct nerve growth stimulated by the thermal energy. For example, the guide template may be a guiding filament (e.g., collagen, laminin or fascia) or a conduit (e.g., a wrapper, a cuff, or a tube) or a surgically prepared tunnel (e.g. laser, electrosurgical cautery, or auger mechanical tunnel). The conduit may be made of various materials derived from natural sources or synthetic materials. The conduit may be biodegradable or non-absorbable. Examples of conduit materials include but not limited to decalcified bone and vessels, fascia lata, fat, muscle, parchment, Cargile membrane, gelatin, agar, rubber, fibrin film, and various metals. The conduit is filled with nerve-growth-stimulating agents such as nerve growth factors.

An apparatus is provided for stimulating nerve growth, especially for regeneration of nerve injured by severance, crush and other physical forces. The apparatus comprises: an applicator including a proximal portion and a distal portion; and energy delivery mechanism that is coupled to the handpiece. The energy delivery mechanism may include an energy delivery surface that controllably delivers a sufficient amount of thermal energy to one or more nerve segments adjacent a damaged region of a nerve and stimulate nerve growth at the treated segments. Preferably, the energy delivery surface controllably delivers the thermal energy to and stimulates growth of one or more nerve segments adjacent the damaged region of the nerve. The amount of thermal energy may be sufficient for heating the segments to a temperature in a range of 41° C. to 58° C., preferably about 44° C. to 55° C. Optionally, the apparatus may include sensor coupled to the energy delivery mechanism, e.g. a temperature sensor for measuring temperature of the nerve segment.

The applicator of the apparatus may be configured to deliver a medium to the distal segment of the nerve, such as electrolyte solution, cooling fluid and medicaments. The applicator may also have a directionally biased distal end.

The energy delivery mechanism of the apparatus may include a variety of probes for delivering various type of energy to the nerve segment. Examples of such probes include but not limited to resistive heating electrodes, RF electrodes, Infrared probes, microwave probe, ultrasound emitters and optical fiber probes that are configured to be coupled to a coherent or incoherent light source configured to be coupled to an ultrasound generator.

The apparatus may optionally include a feedback control mechanism coupled to the energy delivery mechanism. The feedback control mechanism may comprises an energy control signal generator that generates an energy control signal to control energy supplied from an energy source to an energy delivery mechanism; and impedance measurement circuitry coupled to the energy delivery mechanism which measures impedance of a selected site. For example, the impedance measuring circuitry determines a minimum impedance value to determine a target impedance value as a function of the minimum impedance value, compares a measured impedance values to a target impedance value, and alters the control signal when said measured impedance value exceeds the target impedance value.

The apparatus with a feedback control mechanism may further include an energy source configured to supply energy to the energy delivery mechanism. Such an energy source is responsive to control signals directing the energy source to supply energy to the energy delivery mechanism.

The impedance measuring circuitry may includes such devices: a minimum impedance measuring device; a target determining device coupled to the impedance measuring device and configured to determine the target impedance value as a function of the minimum impedance value; and a comparison device for comparing measured impedance values to the target impedance value and generating a signal indicating whether the measured impedance value exceeds the target impedance value. Optionally, the impedance measurement circuitry may include a microprocessor controller.

BRIEF DESCRIPTION OF THE FIGURES

FIG. 2A illustrates a neuroma formation on a terminus of a severed nerve.

FIG. 2B depicts a single terminal segment forming a neuroma.

FIG. 4 illustrates treatment of a portion of the severed nerve by a thermal probe.

DETAILED DESCRIPTION OF THE INVENTION

The present invention provides novel methods and apparatus for stimulating nerve growth, especially for nerve regeneration after damage or severing of the nerve. The method comprises: applying thermal energy to one or more nerve segments adjacent a damaged region of the nerve, such that nerve fibers from the treated segment are stimulated to grow and extend toward the damaged region. The damaged region may be a terminus of a severed nerve, i.e. the proximal or distal end of the nerve resulted from the severance, or a region of nerve not severed yet damaged by crush or other physical forces. The one or more nerve segments may be one nerve segment adjacent the damaged region or a plurality of nerve segments including segments adjacent and distal to the damaged region.

Figure 1B:
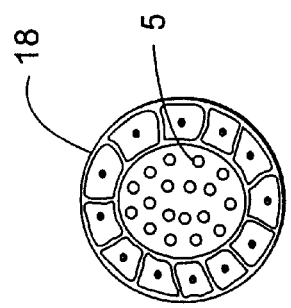
FIG. 1B shows a severed nerve distal terminus in a cross-section.
Figure 1A:
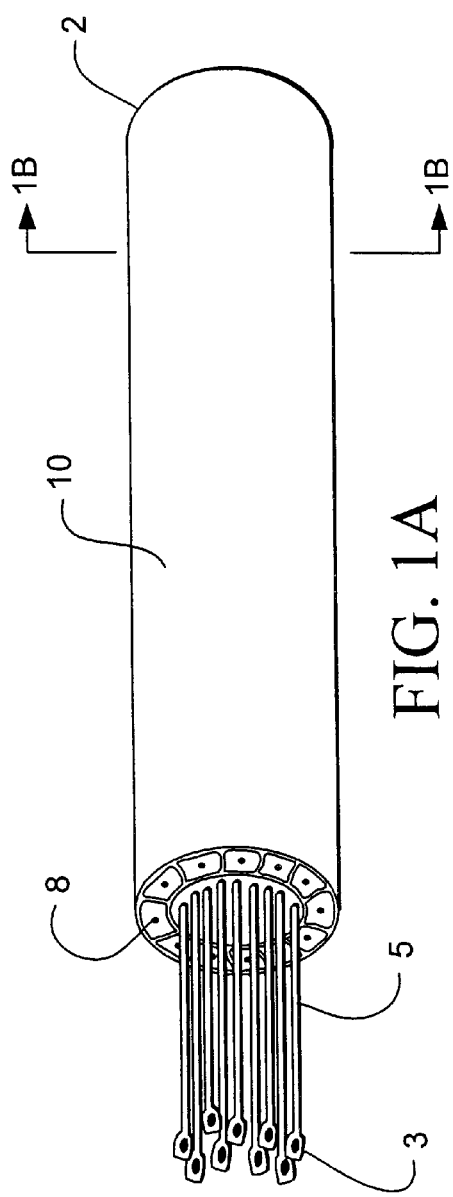
FIG. 1A illustrates an isometric view of a severed nerve with nuclei located within the nerve.

FIG. 1A illustrates a nerve 10 with a myelinated sheath of Schwann cells 8. Numerous nuclei 2 are situated away from a severed distal portion 2 of the nerve. Dendrites 5 extend distally from the nuclei 2. FIG. 1B is a cross-section of the severed nerve 10 along line A—A. Schwann cells 18 are shown composing the myelin sheath and the severed dendrites 15 are illustrated.

Under normal regrowth condition in the body, the severed nerve will begin extending the dendrites to reattach to the corresponding severed nerve for the transmission of nerve stimuli and signals. FIG. 2A a typical severed nerve 20 where the severed dendrites 25 have begun the regrowth process. Without external treatment, extension fibers 27 form at the distal terminus 22. A neuroma consists of a mass of nerve fibers growing irregularly from the injured distal terminus 22 of the nerve. The combination of numerous dendrites 25 growing single segmented extension fibers 27 forms scar tissue or neuroma thereby ceasing further growth and limiting nerve transmission to the nuclei. The formation of neuroma is presumably due to slow growth of nerve fibers, lack of clear pathway for extension and the intervening tissue forming a physical barrier in the gap between the proximal and distal ends of the served nerve. A loss of connection to the corresponding nerve section (not shown) also does not occur. FIG. 2B is a pictorial depiction of a single distal terminus segment 24 growing an extension 27. Without external treatment and stimulus, the distal most terminal segment 24 is only able to grow and extend a short growth 27 leading to the formation of a neuroma or nerve scar tissue.

By external stimulation of at least one segment adjacent the damaged terminus of the nerve, such as by the method and apparatus of the present invention, regeneration of a damaged nerve fiber is enhanced by promoting dendrite extension from the terminus of the severed nerve, yet minimizing the potential of neuroma formation. As illustrated in FIGS. 2A–B, a severing of nerve 20 stimulates axons and/or dendrites of the distal terminus 22 of nerve 20 to grow out. However, as shown in FIGS. 3A–B, the method of the present invention not only enhances this mechanical stimulative effect at the terminus of the damaged nerve, but also retrogrades up the nerve fiber for some distance without destroying the fibers, thereby increasing the response of the injured nerve to regrowth and extension more rapidly.

Figure 3A:
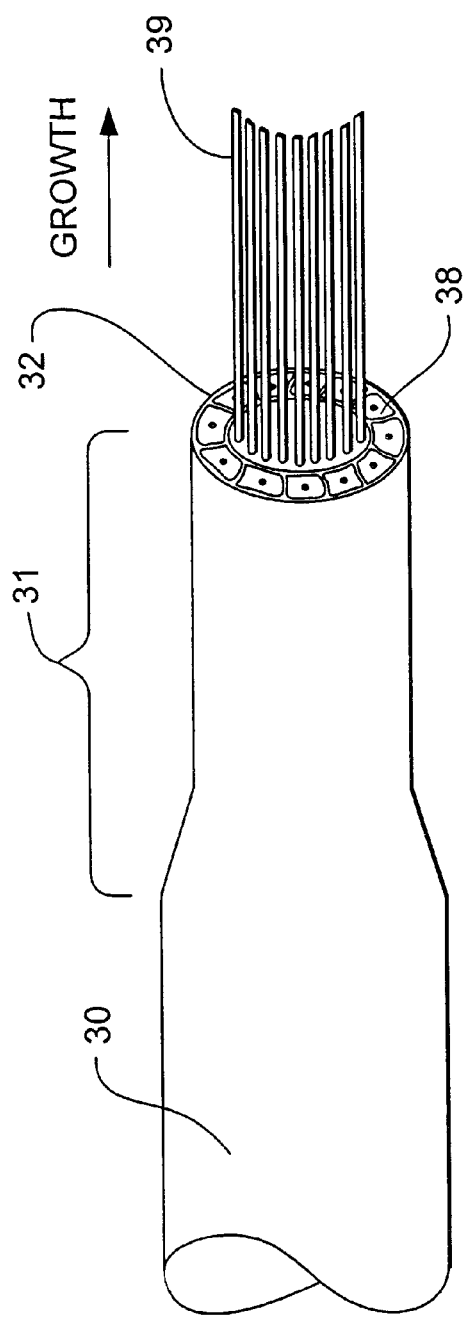
FIG. 3A is a side view of the treated nerve showing a thermal effect along a portion of the distal terminus after treatment.

According to the disclosed invention, FIG. 3A shows a severed distal terminus end 32 of nerve 30. Thermal energy has been applied to treated portion 31 involving several segments of the distal terminus 32. The Schwann cells 38 have slightly denatured in treated portion 31 as illustrated by the indented portion of the distal terminus. The combination of a thermal effect on the Schwann cells 38 and stimulation of numerous distal segments enhances and promotes growth of the dendrites 39 distally from the treated portion 31 towards the corresponding severed nerve (not shown).

Figure 3B:
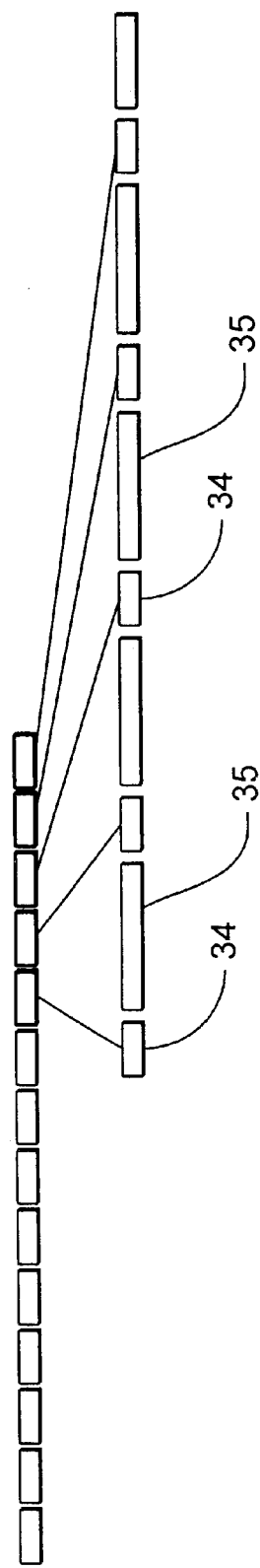
FIG. 3B depicts treatment of distal segments of the nerve terminus showing proportional growth over multiple segments.

As depicted in FIG. 3B, a plurality of segments 36 adjacent and distal to a terminus 32 of a severed nerve 30 is stimulated by thermal energy at low levels. The thermal energy stimulates nerve fibers 34, such as dendrites and/or axons, along the entire course of the distal end of the nerve so that each point along the dendrite itself is stimulated, similar to the mechanical stimulation of regrowth of the severed nerve terminus. Each segment 34 is stimulated to grow out and an exponential telescopic effect is achieved (FIG. 3B) whereby each segment 34 extends out a growth segment 35. As a result, dendrite growth is stimulated across a larger length and at a more rapid rate. The myelin sheath may be somewhat denatured due to heat inactivation of Schwann cells 38. However, the presence of the denatured myelin sheath may also act to provide a natural conduit for some period of time prior to reabsorption and replacement by the body. As illustrated in FIG. 3A, continuous and rapid extension of axon and dendrites 34 should facilitate bridging the gap from the severed distal terminus 32 to the corresponding severed nerve (not shown).

The one or more segments may be a nerve segment adjacent the damaged region, preferably 1–18 mm, more preferably 2–15 mm, and most preferably 2–10 mm from the damaged region. Alternatively, the one or more treated segments may be a plurality of nerve segments located in region adjacent the damaged region, preferably in a region 5 mm to 20 mm distal to the damaged region.

The thermal energy applied to the segments of nerve adjacent the damaged region may be of a sufficient amount for heating the segments to a temperature in a range about 41–58° C., preferably about 44–55° C.

A variety of different energy sources can be used with the present invention to provide the thermal-mechanical stimulation of the nerve, preferably thermal energy from thermal conductive or electromagnetic sources at low energy levels. Examples of thermal conductive energy sources include, but not limited to resistive heating. Alternatively, the thermal energy may be generated by ultrasound or infrared sources. Examples of electromagnetic energy sources include, but not limited to radio frequency (RF) energy, coherent light, incoherent light, microwave and shortwave.

In one embodiment, resistive heating is used to generate thermal energy directly in one or more nerve segments adjacent a damaged region of a nerve. The damaged nerve may be exposed, which allows direct access of a resistive heating electrode coupled to a resistive heating source. Preferably, thermo-resistive heaters with temperature controlling mechanisms may be employed to impart conductive heating across the entire geometry of the nerve segment targeted for treatment. In general, a feedback control mechanism of the resistive heater better controls the temperature on the nerve segment being treated. Feedback control may be achieved by measuring impedance or temperature. By carefully monitoring the temperature on the treated nerve, axons and/or dendrites may be protected from heat damage and stimulated to extend more rapidly.

In one specific embodiment, infrared energy is applied to the treated portion of the distal terminus end adjacent a severed nerve. The penetrating thermal effect of the infrared source provides adequate stimulation of the distal segments of a severed nerve to enhance and promote growth and extension of the dendrites of the nerve.

In another embodiment, RF energy is applied to one or more nerve segments adjacent a damaged region of a nerve. Electrolytic solution and cooling fluid may be utilized to control the amount of thermal energy delivered to the segment. In addition, a feedback control mechanism may be employed to achieve precise control of temperature on the treated nerve. Feedback can be the measurement of impedance or temperature and occurs either at the controller or at the RF source if it incorporates a controller. Impedance measurement can be achieved by supplying a small amount of non-therapeutic RF energy. Voltage and current are then measured to confirm electrical contact.

Generally, electrolytic solution transfers RF energy from an RF electrode to the nerve segment. The cooling fluid may be used to create a thermal gradient at the various levels of the underlying tissue. For example, when thermal energy is applied to the segment adjacent the damaged region superficially, i.e. through the epidermis without directly touching the nerve, RF energy is delivered to the site through the papillary dermis layer, the reticular dermis layer, the subcutaneous layer and the underlying tissue to reach the segment of the damaged nerve. Creating thermal gradient allows precise control of temperature and minimizes burning effects on skin or other tissues.

Other penetrating energy such as light sources that generate heat may also superficially applied to one or more nerve segments adjacent a damaged region of a nerve. The heat effect is preferably confined to the nerve in order to minimizing damaging effects on adjacent tissues. A light pipe or optical fiber may be used to focus coherent or incoherent light down to the segments for stimulating nerve regeneration of the damaged nerve.

For example, laser light may be use to heat one or more nerve segments adjacent a damaged region of a nerve by penetrating the skin and stimulate thermodynamic motion in the treated nerve. When nerve is damaged, neurons start to lose their normal functions, partially due to membrane destabilization. Selective uptake and output of certain ions, proteins, carbohydrate may be impeded, leading to slow down of cellular metabolism and eventual cell death. By providing thermal energy to neurons, axons and dendrites in the nerve, cellular metabolism that is slowed by nerve injury may be restored and the homeostatic energy requirement of nerve growth satisfied.

Compared to direct superficial heating of the tissue above the damaged nerve, superficial application of laser light to stimulate nerve regeneration is advantageous. Superficial directs heating may cause tissue damage over a long application time to deliver thermal energy to nerve deeply buried underneath the tissue. Laser energy, however, can be delivered as photons to tissues below the skin surface without causing superficial heating adverse effects. The wavelength range of the laser light may be selected so as to achieve maximum penetration through the tissue, yet not causing burning effects on the surface tissue. The laser light may be applied to a distal segment of the damage nerve, and continues to irradiate other segments along the course of nerve distal from the damaged site. Along this path, the laser deposits photons into the nerve, which provides homeostatic energy to neurons and stimulate growth of axons and dendrites. Further, micro-circulation may be provided by the application of laser to increase oxygen and blood flow to the damaged nerve, thus expediting recovery of the nerve injury. Therefore, cell growth stimulation, nerve fiber regeneration, revascularization and reduction of neuroma may be achieved by delivery of energy by laser.

In a clinical setting, the treatment of injured nerve, such as served nerve, may include determining the treatment grid area covering one or more nerve segments adjacent a damaged region of a nerve. A permanent marker may also be used to delineate the grid. The treatment skin area may be shaved and or laser energy transmission gel may be applied over the treatment grid. Thereafter, the laser device is activated and held steady during the operating period. After the treatment of one segment, the laser may be directed to irradiate the next distal segment along the course of the nerve. Such operation may be repeated to irradiate a plurality of segments along the nerve fiber until satisfactory results are achieved.

Optionally, the method of present invention may be used in conjunction with conventional funneling procedures and conduit placement modalities to improve success of these procedures. The funneling and conduit techniques provide a template or road map for encouraging nerve growth in a specific direction. For example, regeneration of damaged peripheral nerves (those outside the spinal cord and brain) may be promoted by combining thermal energy delivery and conduit replacement. The conduits may serve as a template for guiding the growth of nerve fiber in the longitudinal orientation of nerve so as to reduce axonal disorganization and restrict the tendency for regenerating axons to escape into extraneural tissue. Stimulation of nerve growth by application of thermal energy may cause rapid extension of axons and dendrites. These sprouts of nerve fibers can be constrained within the transection of a served nerve and prevented from infiltrating into adjacent tissue. Meanwhile, the transection of the served nerve may also be protected from infiltration by adjacent fibrous tissue and prevention. In addition, the potential of neuroma formation may be further reduced by channeling the growing nerve fibers.

The conduit referred herein may be any wrappers, cuffs, or tubes. The conduit may be made of various materials derived from natural sources or synthetic materials. The conduit may be biodegradable or non-absorbable. Examples of conduit materials include, but not limited to decalcified bone and vessels, fascia lata, fat, muscle, parchment, Cargile membrane, gelatin, agar, rubber, fibrin film, and various metals.

For example, the gap between proximal and distal ends of a severed nerve may be brought into contact with each end of a hollow conduit whose walls are comprised of a matrix of Type I collagen and laminin-containing material. When thermal energy is applied to distal segments of the served nerve, greater numbers of regenerating axons may be stimulated (many of which may become myelinated), a substantial increase in the initial rate of the outgrowth of fibers and myelinated axons may be produced. Such rapidly regenerating axons and dendrites may be able to span even longer gaps than just applying thermal energy to the distal ends, presumably due to the absence of a filling in the center of the tube which may tend to impede the growth of the nerve fibers and axons through the center thereof.

Optionally, a nerve graft with nerve regeneration promoting substances or components to further promote regeneration of the injured nerve. Examples of nerve regeneration promoting substances include but not limited to fibronectin, laminin angiogenesis factors, nerve growth factors, extracts of central nervous tissue, and Schwann cells.

By using these combination treatments according to the present invention, rapid nerve growth is achieved; longitudinal alignment of nerve tissue is provided; extraneural fibrous invasion is eliminated; and extrafascicular sprouting of axons is eliminated. Additionally, a regenerated nerve is consistently obtained growing in a central location down the lumen of the nerve conduit and innervating the distal nerve stump. Blood vessels are reformed and a tremendous amount of growth occurs. In addition, Schwann cells (nonneuronal cellular elements that provide structural support and insulation to nerve endings) may be allowed to travel farther along the gap than they would when either treatment is used alone.

The present invention also provides apparatus for stimulating nerve growth, especially for regeneration of nerve injured by severance, crush and other physical forces. In one embodiment, the apparatus comprises: an applicator including a proximal portion and a distal portion; and energy delivery mechanism that is coupled to the handpiece.

The energy delivery mechanism according to the present invention may include an energy delivery surface that controllably delivers a sufficient amount of thermal energy to one or more nerve segments adjacent and/or distal to a damaged region of a nerve and stimulate nerve growth at the treated segments. Preferably, the energy delivery surface controllably delivers the thermal energy to and stimulates growth of one or more nerve segments adjacent the damaged region of the nerve. The amount of thermal energy may be sufficient for heating the segments to a temperature in a range of 41° C. to 58° C., preferably about 44° C. to 55° C. Optionally, the apparatus may include sensor coupled to the energy delivery mechanism, e.g. a temperature sensor for measuring temperature of the nerve segment.

The applicator of the apparatus may be configured to deliver a medium to the distal segment of the nerve, such as electrolyte solution, cooling fluid and medicaments. The applicator may also have a directionally biased distal end.

The energy delivery mechanism of the apparatus may include a variety of probes for delivering various type of energy to the nerve segment. Examples of such probes include but not limited to resistive heating electrodes, RF electrodes, Infrared probes, microwave probe, ultrasound emitters and optical fiber probes that are configured to be coupled to a coherent or incoherent light source configured to be coupled to an ultrasound generator.

The apparatus may optionally include a feedback control mechanism coupled to the energy delivery mechanism. The feedback control mechanism may comprises an energy control signal generator that generates an energy control signal to control energy supplied from an energy source to an energy delivery mechanism; and impedance measurement circuitry coupled to the energy delivery mechanism which measures impedance of a selected site. For example, the impedance measuring circuitry determines a minimum impedance value to determine a target impedance value as a function of the minimum impedance value, compares a measured impedance values to a target impedance value, and alters the control signal when said measured impedance value exceeds the target impedance value.

The apparatus with a feedback control mechanism may further include an energy source configured to supply energy to the energy delivery mechanism. Such an energy source is responsive to control signals directing the energy source to supply energy to the energy delivery mechanism.

The impedance measuring circuitry may includes such devices: a minimum impedance measuring device; a target determining device coupled to the impedance measuring device and configured to determine the target impedance value as a function of the minimum impedance value; and a comparison device for comparing measured impedance values to the target impedance value and generating a signal indicating whether the measured impedance value exceeds the target impedance value. Optionally, the impedance measurement circuitry may include a microprocessor controller.

FIG. 4 illustrates an apparatus according to the present invention. Probe 100 may be configured to be used in an open procedure such as in open surgery to reattach and reapproximate larger nerves or in an arthroscopic or microscopic surgical environment through the use of viewing scopes or microscopes (not shown). The probe 100 has a handle for connection to an energy source and a shaft 102. The probe shaft 102 has an energy delivery portion 105 at the distal portion of the shaft for delivery of thermal or electromagnetic energy to treatment site 41 on a distal terminus 42 of nerve 40. Dendrites 45 are shown extending from the nuclei of the nerve cell through to the severed distal terminus 42. The myelin sheath is composed of Schwann Cells 48.

The treatment portion 41 may be 2–10 mm from the damaged region. Alternatively, the one or more treated segments may be a plurality of nerve segments located in region adjacent the damaged region, preferably in a region 5 mm to 20 mm distal to the damaged region.

The thermal energy applied to treatment portion 41 by probe 100 to the damaged region may be of a sufficient amount for heating the segments to a temperature in a range about 44–55° C. A temperature feedback control circuit may be incorporated at the tip of energy delivery portion 105 to precisely control the energy delivered to treatment portion 41. The feedback control circuit may incorporate a thermocouple within the distal portion of the shaft at or near the tip of the energy delivery portion 105. The thermocouple acts as a temperature sensor for the probe. Thermistors and other temperature sensor devices such as integrated circuit temperature sensors may also be used. A microprocessor control (not shown) may be incorporated to control the energy delivery of probe 100 to precisely control the energy delivery and temperature.

EXAMPLE

In experiments where animals are treated by using the method and apparatus according to the present invention, a 1 cm segment of the sciatic nerve was severed. Upon reexamination several weeks after sciatic nerve dissection a majority of subjects were found to have significant extension (greater than 1 cm) of the severed nerved. Untreated controls demonstrates only minimal growth and in some instances neuroma formation. Extension of dendrites is thereby promoted outward from the severed nerve.

The dendrites are stimulated along the entire course of the distal end of the nerve that is treated. Each part then is stimulated to grow out and a telescoping effect is achieved. This extends dendrite growth across at a much greater or more rapid rate then by just stimulating the end of the nerve.

Stimulating the distal segment of the nerve instead of just the terminus with non-ablating energies stimulates a greater portion of the nerve without denaturing the nerve. There is some shrinkage and denaturation of the myelin sheath. However, this tissue regenerates quickly without sequela.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A method for enhancing growth of a nerve, comprising:

applying thermal energy to one or more nerve segments adjacent a damaged region of the nerve, such that nerve fibers from the treated segments are stimulated to grow and extend toward the damaged region.

2. The method according to claim 1, wherein the damaged region of the nerve is a terminus of a severed nerve.

3. The method according to claim 1, wherein the damaged region of the nerve is a region of a crushed nerve.

4. The method according to claim 1, wherein applying thermal energy to the one or more segments includes applying thermal energy to a segment about 1–18 mm distal to the damaged region.

5. The method according to claim 1, wherein applying thermal energy to the one or more segments includes applying thermal energy to successive segments of nerve adjacent and distal to the damaged region.

6. The method according to claim 5, wherein applying thermal energy to the one or more segments includes applying thermal energy to successive segments of nerve about 1–18 mm distal to the damaged region.

7. The method according to claim 5, wherein applying thermal energy to the one or more segments includes applying thermal energy to successive segments of nerve about 2–15 mm distal to the damaged region.

8. The method according to claim 5, wherein applying thermal energy to the one or more segments includes applying thermal energy to successive segments of nerve about 2–10 mm distal to the damaged region.

9. The method according to claim 1, wherein applying thermal energy to the segments includes applying thermal energy superficially to the segments adjacent the damaged region of the nerve.

10. The method according to claim 1, wherein the thermal energy is generated from an electromagnetic energy source.

11. The method according to claim 7, wherein the electromagnetic source is selected from the group consisting of radio frequency energy, coherent light, incoherent light, microwave and shortwave.

12. The method according to claim 1, wherein the thermal energy is generated from a thermal conductive source.

13. The method according to claim 12, wherein thermal conductive source is a resistive heating source.

14. The method according to claim 1, wherein applying thermal energy to the segments includes heating the segments to a temperature range of about 41° C. to 58° C.

15. The method according to claim 1, wherein applying thermal energy to the segments includes heating the segments to a temperature range of about 44° C. to 55° C.

16. The method according to claim 1 further comprises:

placing a guide template over the damaged region to direct nerve growth stimulated by the thermal energy.

17. The method according to claim 16, wherein the guide template is a conduit.

18. The method according to claim 16, wherein the conduit is filled with nerve-growth-stimulating agents.

19. The method according to claim 16, wherein the guide template is guiding filament.

20. The method according to claim 19, wherein the guiding filament is collagen, laminin or fascia.

* * * * *